(12) United States Patent
Yang et al.

(10) Patent No.: US 10,247,750 B2
(45) Date of Patent: Apr. 2, 2019

(54) ONLINE MEASURING METHOD OF PARTICLE VELOCITY IN MULTIPHASE SYSTEM

(71) Applicants: INSTITUTE OF PROCESS ENGINEERING, CHINESE ACADEMY OF SCIENCES, Beijing (CN); Nanjing Jiuzhang Chemical Technology Co., Ltd., Jiangsu (CN)

(72) Inventors: Chao Yang, Beijing (CN); Xiangyang Li, Beijing (CN); Haoliang Wang, Beijing (CN); Guanqi Wang, Beijing (CN); Zaisha Mao, Beijing (CN)

(73) Assignees: INSTITUTE OF PROCESS ENGINEERING, CHINESE ACADEMY OF SCIENCES (CN); NANJING JIUZHANG CHEMICAL TECHNOLOGY CO., LTD. (CN)

( * ) Notice: Subject to any disclaimer, the term of this patent is extended or adjusted under 35 U.S.C. 154(b) by 165 days.

(21) Appl. No.: 15/368,804

(22) Filed: Dec. 5, 2016

(65) Prior Publication Data

US 2017/0299620 A1 Oct. 19, 2017

(30) Foreign Application Priority Data

Apr. 19, 2016 (CN) .......................... 2016 1 0244969

(51) Int. Cl.
*H04N 7/18* (2006.01)
*G01P 3/38* (2006.01)
(Continued)

(52) U.S. Cl.
CPC ............ *G01P 3/38* (2013.01); *G01N 15/1429* (2013.01); *G01N 15/1463* (2013.01); *G01P 5/20* (2013.01);
(Continued)

(58) Field of Classification Search
CPC ................................ G01P 3/38; H04N 5/2354
(Continued)

(56) References Cited

U.S. PATENT DOCUMENTS 6,879,708 B2 * 4/2005 Wernet ...................... G06T 7/62
356/28
2006/0116531 A1 * 6/2006 Wonders ............... C07C 51/265
562/412

(Continued)

*Primary Examiner* — Richard T Torrente
(74) *Attorney, Agent, or Firm* — McDonald Hopkins LLC

(57) ABSTRACT

The present invention provides an online measuring method of particle (such as bubbles, droplets and solid particles) velocity in multiphase reactor. The method based on an online multiphase measuring instrument includes the following steps: (1) the online multiphase measuring instrument is placed into the multiphase reactor, and then a particle image produced by two or more exposures are obtained; (2) the actual size of individual pixel in the particle image is determined; (3) valid particles are determined in the depth of field; (4) then the centroid coordinates are conversed to the actual length of the coordinates $(x_{t,i}, y_{t,i})$ and $(x_{t+\Delta t,i}, y_{t+\Delta t,i})$ using the actual size of individual pixel. Thus, the instantaneous velocity of particles can be calculated by $$V_i = \sqrt{\frac{(x_{t+\Delta t,i} - x_{t,i})^2 + (y_{t+\Delta t,i} - y_{t,i})^2}{\Delta t}}.$$

The method can realize real-time measurement of the velocity distribution of bubbles, droplets or solid particles in a multiphase reactor, and the measurement accuracy is high.

20 Claims, 3 Drawing Sheets

(51) Int. Cl.
| | |
|---|---|
| *G01N 15/14* | (2006.01) |
| *H04N 5/235* | (2006.01) |
| *G01P 5/20* | (2006.01) |
| *G01P 5/22* | (2006.01) |
| *G01N 15/10* | (2006.01) |
| *G01N 15/00* | (2006.01) |

(52) U.S. Cl.
CPC ............. *G01P 5/22* (2013.01); *H04N 5/2353* (2013.01); *H04N 5/2354* (2013.01); *G01N 2015/0026* (2013.01); *G01N 2015/0046* (2013.01); *G01N 2015/0053* (2013.01); *G01N 2015/1075* (2013.01); *G01N 2015/1493* (2013.01)

(58) Field of Classification Search
USPC ........................................................ 348/137
See application file for complete search history.

(56) References Cited

U.S. PATENT DOCUMENTS

2011/0310270 A1* 12/2011 Gladnick ........... G01N 21/8806
348/229.1
2013/0057675 A1* 3/2013 Jaaskelainen ............. G01P 5/22
348/84

* cited by examiner

ONLINE MEASURING METHOD OF PARTICLE VELOCITY IN MULTIPHASE SYSTEM

The present application claims priority to and the benefit of Chinese Patent Application No. 201610244969.2 filed on Apr. 19, 2016, the entire disclosure of which is incorporated herein by reference in its entirety.

TECHNICAL FIELD

The present invention belongs to the field of physical measuring technology, involving a new measuring method of dispersed phase particle velocity in multiphase reactor.

BACKGROUND ART

In chemistry, metallurgy, environment and other industry, complex coupled processes including multiphase flow, mass transfer, heat transfer and reaction are often involved in which the flow is the basis for all the other processes, and will largely determine the efficiency of other processes. Thus, velocity measurement of multiphase flow is very important for industrial reactor design, optimization and amplification.

Although the fluid velocity measurement technologies have been greatly developed, there is still a huge challenge in multiphase flow velocity. At the early stage, pitot tube and thermal anemometer are mainly uses. For pitot tube, the dynamic response frequency is so low that the information of high-frequency pulse in unsteady turbulent field cannot be recorded. High viscosity liquid or fine solid particles will clog pitot probe. So its application has certain limitations. Thermal anemometer is divided into hot wire anemometer and hot film anemometer. Hot wire anemometer has high frequency response, high sensitivity, large dynamic range and small size of the probe. But the probe and sensor are easily broken in a strong vortex containing particles. In addition, high viscosity liquid is easier to stick on the probe surface which affects measurement accuracy. Hot film anemometer is relatively solid and wear-resisting, but its frequency response is low.

The development of laser technology promotes the rapid development of the laser doppler velocimetry (LDV) and particle image velocimetry (IV). LDV, because of its high precision and fast response, has been widely used in gas-solid, gas-liquid, solid-liquid flow experiments. But the LDV has strict requirements for the concentration of measured solid phase particles or fluid tracer. At the same time, complex instrument calibration needs to be done before it is used. PIV can get the instant information of the whole flow field in unsteady flow. But due to the complexity of multiphase flow of tracer particles, PIV technique is usually used only to measure the liquid phase velocity in multiphase flow. Particle tracking velocimetry (PTV) is a special kind of PIV, which can calculate the velocity by tracking the trajectory of individual particle and achieve high spatial precision. But the current PTV technique has great demands on measured flow channel, tracer or dispersed particles and image processing.

Therefore, the measuring method of the particle velocity in multiphase reactors has yet to be further studied.

SUMMARY OF THE INVENTION

In view of the problems existing in the prior techniques, the purpose of the present invention is to provide an online measuring method of particle velocity in multiphase reactors. The method described herein uses an online multiphase measuring instrument, and combines with the multiple-exposure technique and image processing method, then realizes the measurement of velocity distribution of bubbles, droplets or solid particles in multiphase reactors. The measurement accuracy is high.

In order to achieve this goal, the present invention adopts the following technical scheme:

An online measuring method of particle velocity in multiphase system based on an online multiphase measuring instrument, wherein the online multiphase measuring instrument includes:

a package tube;

a viewport, sealedly installed at the front end of the package tube;

an illumination system for illuminating multiphase flow, including LED lamps and a brightness-adjustable light source connected with the LED lamps, which comprises a power supply, a signal generator and an oscilloscope;

a photographic system for taking pictures, including a telecentric lens and an image sensor;

a controller connected with the signal generator and the image sensor;

a signal processing and outputting system connected with the image sensor;

a display system connected with the signal processing and outputting system.

The LED lamps, the telecentric lens and the image sensor are located in the package tube and the exposure period of the image sensor is greater than the pulse period of the signal generator, controlled by the controller.

The measuring method described herein includes the following steps:

(1) the online multiphase measuring instrument is placed in a multiphase system, the exposure time $t_1$ of the image sensor and the pulse period $t_2$ of the signal generator are controlled to meet the condition $t_1 > 2t_2$, and a double-exposure particle image is obtained;

(2) the actual size of individual pixel in the image is determined;

(3) valid particles are determined using the following steps: first, the focal plane position of the telecentric lens is determined; then, the object to be measured is respectively arranged on the front of the package tube, the l/2 positions ahead of or behind the focal plane, where l is the telecentric lens depth of field in mm; the object to be measured is photographed by the online multiphase measuring instrument, and the image of the object is obtained and the gray gradient Grad($\Phi_{l/2}$) around the boundary of the object is determined, where $\Phi_{l/2}$ is the gray value at the ±l/2 positions ahead of or behind the focal plane; if Grad($\Phi$) is greater than or equal to Grad($\Phi_{l/2}$), the particle is labeled as a valid one; and (4) the double-exposure image of the same valid particle is identified; the lower left corner of the particle image is set as coordinate origin; in accordance with the order "binarization, interception of part of the area and centroid extraction", the centroid coordinates $(m_{t,i}, n_{t,i})$ and $(m_{t+\Delta t,i}, n_{t+\Delta t,i})$ are read; then the centroid coordinates are conversed to the actual length of the coordinates $(x_{t,i}, y_{t,i})$ and $(x_{t+\Delta t,i}, y_{t+\Delta t,i})$ using the actual size of individual pixel obtained in step (2), so the instantaneous velocity of particles is calculated by:

$$V_i = \sqrt{\frac{(x_{t+\Delta t,i} - x_{t,i})^2 + (y_{t+\Delta t,i} - y_{t,i})^2}{\Delta t}},$$

where Δt is the time interval between two exposures. The locations of the coordinates selected in step (4) are arbitrary, and preferably, centroid coordinates are positive as they are selected.

The centroid coordinates of the same particle in two exposures are the centroid coordinates of the particle in the first and second exposure, respectively.

As depicted in Step (1), the exposure time of the image sensor is 2.7-3.0 times of the pulse period of the signal generator, such as 2.8 times or 2.9 times. Preferably, it is 2.8 times.

As depicted in Step (2), a graduated ruler with an accuracy of at least 0.1 mm is used to determine the actual size of individual pixel, such as an accuracy of 0.05 mm or 0.01 mm, etc. Specifically, the number of pixels per unit length is calculated according to the total number of pixels of the image.

The double-exposure image of the same valid particle is identified by a particle matching algorithm in Step (4).

A particle correlation algorithm is used to conduct time-matching of the particles in the particle matching algorithm.

The distribution of the average flow field of the particle velocity in the multiphase system can be obtained by means of averaging the instantaneous velocity based on a particle image containing at least 4000 particles for a period of time.

The particle image depicted in Step (1) is an image of any one selected from the group consisting of bubbles, droplets or solid particles in a multiphase system, or a combination of at least two selected therefrom.

The work distance of the telecentric lens is 250-550 mm in order that the probe can achieve everywhere in the multiphase reactor, such as 260 mm, 300 mm, 350 mm, 380 mm, 420 mm, 470 mm, 550 mm and so on, and the depth of field is 1-3.7 mm, such as 1.2 mm, 1.5 mm, 1.8 mm, 2.0 mm, 2.2 mm, 2.5 mm, 2.8 mm, 3.0 mm or 3.5 mm and so on.

In order to disturb the flow field as less as possible, the magnification of the telecentric lens can be abandoned a little. Preferably, the magnification of the telecentric lens is 0.5-1 time, such as 0.6 times, 0.7 times, 0.8 times or 0.9 times.

The external diameter of the telecentric lens is 19-25 mm, such as 20 mm, 21 mm, 22 mm, 23 mm or 24 mm, etc.

The image sensor is a CCD camera or a CMOS camera.

The exposure time of the CCD camera or CMOS camera is less than or equal to 1 ms, such as 0.1 ms, 0.5 ms, 1 ms and so on. The resolution of it is 5-15 μm, such as 10 μm, 12 μm, 14 μm, 15 μm and so on. The number of pixels in length and width is at least 800×600, such as 2560×1920, 2048×1536, 1600×1200, 1280×1024, 800×600 and so on. The frame frequency is at least 60 fps, such as 60 fps, 100 fps, 150 fps, 200 fps, 1000 fps and so on.

The LED lamps of the photographic probe are inside the package tube, while the brightness-adjustable light source is outside. Pulse light with various wavelengths for different multiphase systems is obtained by adjusting the light source. The number of the LED lamps is at least 12, such as 12, 16, 20, 24 and so on.

The LED lamps are evenly arranged circularly in the package tube. The internal diameter of the circular LED lamps should be as small as possible in the premise of the brightness.

The LED lamps are linked with the brightness-adjustable light source through wires.

The package tube is composed of a front tube and a back tube with different diameters.

The external diameter of the front tube is 25-30 mm, such as 25 mm, 26 mm, 28 mm and so on, and the length is 300-600 mm, such as 320 mm, 350 mm, 400 mm, 450 mm, 500 mm, 550 mm, 600 mm and so on. Specific size of the front tube can be determined according to the parameters of the selected telecentric lens by one skilled in the art.

The external diameter of the back tube is 50 mm, and the length is 50 mm. Specific size of the back tube can be determined according to the size of the selected image sensor by one skilled in the art.

The material of the package tube is stainless steel.

The viewport, LED lamps and telecentric lens are packaged in the front tube. The viewport is arranged on the end of the front tube away from the back tube, followed by the LED lamps and telecentric lens and the image sensor (CCD or CMOS camera) is packaged in the back tube.

The viewport is made up of a piece of circular glass coated by antireflection film inside, which can make sure the light transmittance over 95%.

The signal generator and the image sensor are connected to the controller by a high-speed data line to realize high speed transmission of the image.

The display system comprises an LED screen. It is used to display a signal received from a signal processing and outputting system.

The signal processing and outputting system, the controller and the display system are integrated into a computer. The computer can realize the functions of the signal processing and outputting system, controller and display system.

Images with almost no distortion are obtained using the online multiphase measuring instrument based on telecentric photography because of its unique optical. Its work distance is so long that it can extend everywhere in a multiphase reactor. The particle velocity in a two-phase or three-phase system can be measured online using a simple image processing method by coupling multi-frames measurement taken by online (or single image obtained by multiple exposure).

Compared with the prior technologies, the present invention has the following beneficial effects:

A measuring method for particle velocity in a multiphase reactor is provided in the invention. Using an online multiphase measuring instrument based on the coupling of multiple exposure technique and particle matching algorithm, real-time measurement of bubble, droplet or solid particle velocity distribution can be achieved in the multiphase reactor. According to the invasive error analysis based on CFD simulation, the measuring error for the particle velocity error is less than 15%.

BRIEF DESCRIPTION OF THE DRAWINGS

As shown in FIG. 1, "1" is a viewport, "2" is LED lamps, "3" is a stainless steel package tube, "4" is a telecentric lens, "5" is a minisize fast speed CMOS camera, "6" is a brightness-adjustable light source, "7" is a wire, "8" is a USB3.0 data line, "9" is a fast speed image acquisition card, and "10" is a sampling computer.

EMBODIMENTS

Further description of the technical scheme is as follows by specific examples combining with the drawings.

Example 1

Figure 1:
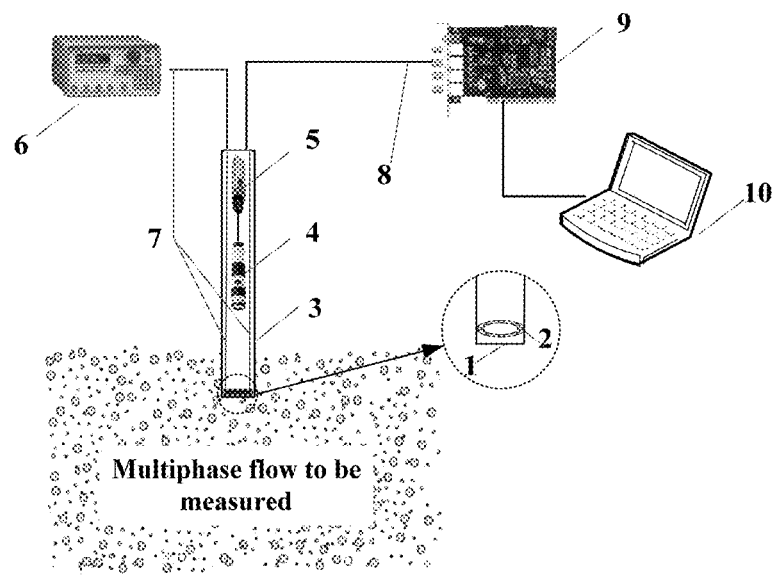
FIG. 1 is a schematic drawing of the structure of the immersion-type online multiphase measuring instrument provided in Example 1 according to the present invention.

The online multiphase measuring instrument includes, as shown in FIG. 1:
a stainless steel package tube 3;
a viewport 1, sealedly installed at the front end of the stainless steel package tube 3;
an illumination system for illuminating multiphase flow, including LED lamps 2 and a brightness-adjustable light source connected with the LED lamps 2, which comprises a power supply, a signal generator and an oscilloscope;
a photographic system for taking pictures, including a telecentric lens 4 and an image sensor; the image sensor is a high speed CMOS camera 5;
a controller connected with the signal generator and the image sensor;
a signal processing and outputting system connected with the image sensor; and
a display system connected with the signal processing and outputting system.

The LED lamps, the telecentric lens and the image sensor are located in the stainless steel package tube, the brightness-adjustable light source, the controller, the signal processing and outputting system and the display system are located outside the stainless steel package tube, and the exposure period of the image sensor is greater than the pulse period of the signal generator, controlled by the controller.

The signal processing and outputting system, the controller and the display system are integrated into a sampling computer 10.

Specifically, the first element is a viewport 1, which is a piece of circular sapphire glass coated by antireflection film. Twenty LED lamps 2 are arranged uniformly behind the viewport 1, which composes a ring. A telecentric lens 4 is installed behind the LED lamps 2, and the parameters are listed as: the magnification is 1; both vision fields of objects and images are ϕ8 mm; the work distance is 250 mm; the telecentricity is less than 0.1°; the depth of field is 2.1 mm; the resolution is 14.3 μm and the optical aberration is less than 0.12%. A work distance is between the outside surface of the viewport and the front side of the telecentric lens 4, in order to take sharp pictures. A standard C port connects the telecentric lens 4 to the high speed CMOS camera 5. Parameters of the CMOS camera 5 are that the resolution is 1280×1024, the colors are monochrome, the frame rate is 150 fps and a USB 3.0 is applied. The viewport 1, the LED lamps 2, the telecentric lens 4 and the high speed CMOS camera 5 are packaged inside the stainless steel package tube 3. A brightness-adjustable light source 6 is configured outside of the measuring instrument, connecting to the LED lamps 2 by a wire 7. The telecentric lens 4 connects to the sampling computer 10 by a USB3.0 data line 8, and the computer is equipped with high speed image acquisition card.

Figure 2:
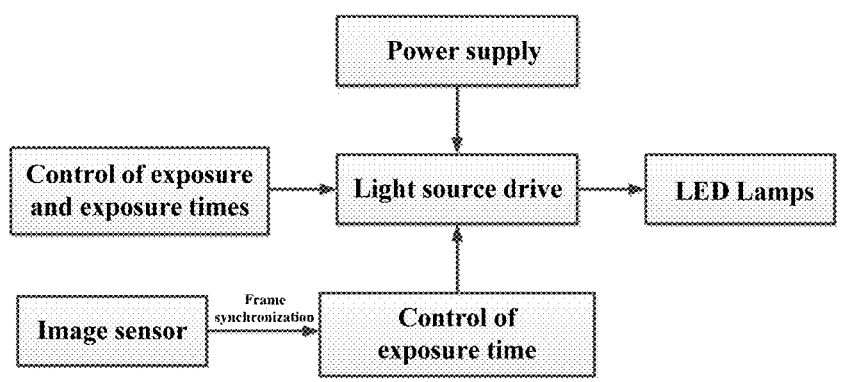
FIG. 2 is a synchronization control mode of lighting flash and CCD camera provided in Example 1.

In order to obtain a clear image by such an instrument, the way to control the synchronization of LED lamps 2 flashing and CMOS camera 5 is shown in FIG. 2: opening source switch, then setting the intensity and period of pulse light by the light source driver; next, setting the exposure time, light balance, frame rate and gain to match the pulse period of the illumination signal and the exposure time of the image sensor (the exposure period of the image sensor is greater than the pulse period of the signal generator) by the controller in computer. Thus, the synchronization of pulse light and image capturing is realized.

Example 2

Velocity distribution of solid particles in liquid-solid system is measured by the online multiphase measuring instrument depicted in Example 1.

The experiment was carried out in an elliptical-bottom plexiglass stirred tank with an inner diameter of T=280 mm stirred by a six-leaf pitched-blade turbine with a diameter of D=T/3 with 4 standard baffles (the baffle width B=T/10). The turbine height off bottom is C=T/3. The impeller speed is 480 rpm. Static liquid height is H=1.2T. The average solid holdup (volume ratio) is 0.01. The measured points are at r=0.025, 0.045, 0.065, 0.085, 0.105, 0.125 m, and z=0.045, 0.090, 0.135, 0.180, 0.220, 0.260, 0.300 m.

Figure 3:
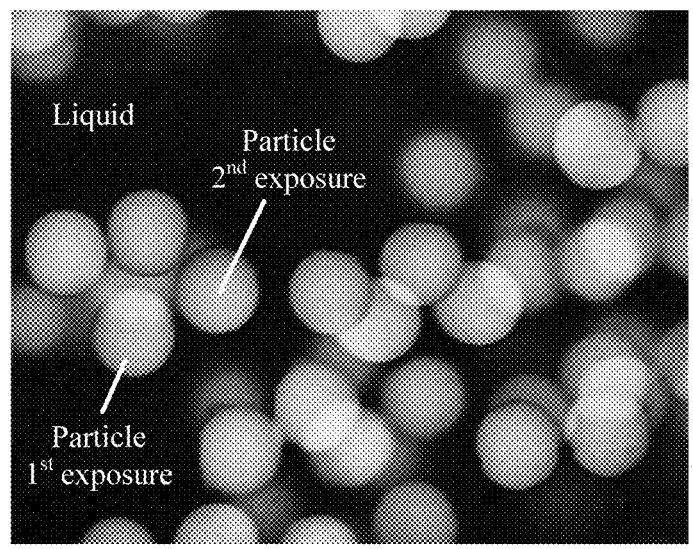
FIG. 3 is a double-exposure image of the liquid-solid system provided in Example 2.
Figure 4:
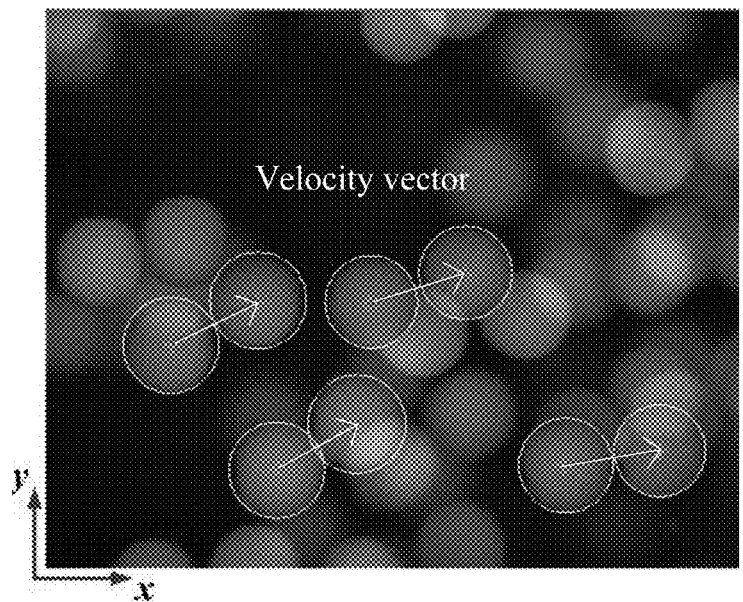
FIG. 4 is a processed result of the double-exposure image in FIG. 3.

The measuring method includes the following steps:
(1) the online multiphase measuring instrument is placed in a multiphase reactor; the exposure time $t_1$ of the image sensor and the pulse period $t_2$ of the signal generator are controlled to meet the condition $t_1>2t_2$, and a double-exposure particle image is obtained, as shown in FIG. 3;
(2) the actual size of individual pixel in the image is calibrated using a graduated ruler with an accuracy of 0.1 mm scale;
(3) valid particles are determined using the following steps: first, the focal plane position of the telecentric lens is determined; then, the object to be measured is respectively arranged on the front of the package tube, the l/2 positions ahead of or behind the focal plane, where l is the telecentric lens depth of field (mm); the object to be measured is photographed by the online multiphase measuring instrument, and the image of the object is obtained and the gray gradient Grad($\Phi_{l/2}$) around the boundary of the object is determined, where $\Phi_{l/2}$ is the gray value at the ±l/2 positions ahead of or behind the focal plane; if Grad($\Phi$) is greater than or equal to Grad($\Phi_{l/2}$), the particle is labeled as a valid one; and
(4) the double-exposure image of the same valid particle is identified using a particle matching algorithm; the lower left corner of the particle image is set as coordinate origin; in accordance with the order "binarization, interception of part of the area and centroid extraction", the centroid coordinates $(m_{t,i}, n_{t,i})$ and $(m_{t+\Delta t,i}, n_{t+\Delta t,i})$ are read; then the centroid coordinates are conversed to the actual length of the coordinates $(x_{t,i}, y_{t,i})$ and $(x_{t+\Delta t,i}, y_{t+\Delta t,i})$ using the actual size of individual pixel obtained in step (2), so the instantaneous velocity of particles is calculated by:

$$V_i = \sqrt{\frac{(x_{t+\Delta t,i} - x_{t,i})^2 + (y_{t+\Delta t,i} - y_{t,i})^2}{\Delta t}},$$

where $\Delta t$ is the time interval between two exposures.

Figure 5:
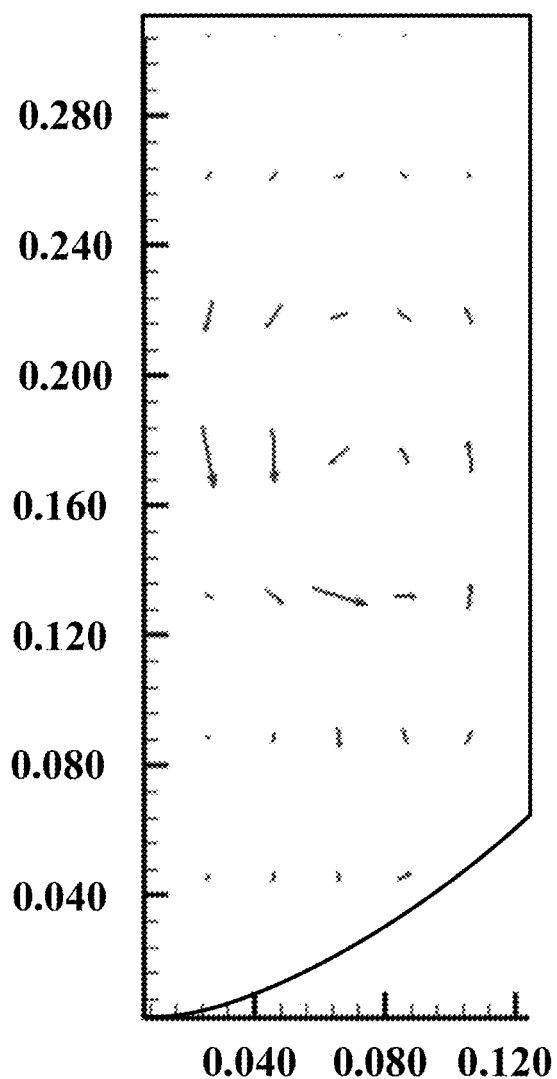
FIG. 5 is a velocity profile of the solid particle obtained by the measuring method of particle velocity in Example 2.

According to the analysis of nearly 4000 particles, the velocity distribution of solid particles in liquid-solid system is shown in FIG. 5. Compared to the CFD simulation of the invasive error analysis, all of the errors of measuring results are less than 15%.

The velocity measuring methods of droplets and bubbles are the same as that of solid particles.

Those skilled in the art to which the present invention belongs should appreciate that the exposure time of the image sensor is 2.7-3 times of the pulse cycle of the signal generator, the work distance of the telecentric lens is 250-550 mm, the depth of fields is 1-3.7 mm, the magnification of the telecentric lens for 0.5-1 times, the diameter of the telecentric lens is 19-25 mm, the number of the LED lamps is greater or equal to 12, the outer diameter of the front pipe is 25-30 mm, the length of the front pipe is 300-600 mm, the pipe diameter of the back pipe is 50 mm, and the length of the back pipe is 50 mm in Example 1.

Those skilled in the art to which the present invention belongs should appreciate that the exposure time of the image sensor is 2.7-3 times of the pulse cycle of the signal generator in step (1), and the resolution of the scale can be 0.05 mm or 0.01 mm in step (2), and the particle matching algorithm can be Sequential Similarity Detection Algorithm in step (4) for Example 2.

The above are only specific examples of the present invention but the present invention is not limited thereto. Those skilled in the art to which the present invention belongs should appreciate that any change or replacement which can be easily thought by those skilled in the art within the technical scope disclosed by the present invention all fall into the scope protected and disclosed by the present invention.

The invention claimed is:

1. An online measuring method of particle velocity in multiphase system, based on an online multiphase measuring instrument comprising:
    a package tube;
    a viewport, sealedly installed at a front end of the package tube;
    an illumination system for illuminating multiphase flow, including LED lamps and a brightness-adjustable light source connected with the LED lamps, which comprises a power supply, a signal generator and an oscilloscope;
    a photographic system for taking pictures, including a telecentric lens and an image sensor;
    a controller connected with the signal generator and the image sensor;
    a signal processing and outputting system connected with the image sensor;
    a display system connected with the signal processing and outputting system;
    the LED lamps, the telecentric lens and the image sensor are located in the package tube and the exposure period of the image sensor is greater than the pulse period of the signal generator, controlled by the controller;
    wherein the measuring method includes the following steps:
    (1) the online multiphase measuring instrument is placed in a multiphase system; the exposure time $t_1$ of the image sensor and the pulse period $t_2$ of the signal generator are controlled to meet the condition $t_1 > 2t_2$, and a double-exposure particle image is obtained;
    (2) the actual size of individual pixel in the image is determined;
    (3) valid particles are determined using the following steps: first, the focal plane position of the telecentric lens is determined; then, an object to be measured is respectively arranged on the front of the package tube, the l/2 positions ahead of or behind the focal plane, where l is the telecentric lens depth of field in mm; the object to be measured is photographed by the online multiphase measuring instrument, and the image of the object is obtained and a gray gradient $Grad(\Phi_{l/2})$ around the boundary of the measured object is determined, where $\Phi_{l/2}$ is the gray value at the ±l/2 positions ahead of or behind the focal plane; if $Grad(\Phi)$ is greater than or equal to $Grad(\Phi_{l/2})$, the particle is labeled as a valid one;
    (4) the double-exposure image of the same valid particle is identified; the lower left corner of the particle image is set as coordinate origin; in accordance with the order "binarization, interception of part of the area and centroid extraction", the centroid coordinates $(m_{t,i}, n_{t,i})$ and $(m_{t+\Delta t,i}, n_{t+\Delta t,i})$ are read; then the centroid coordinates are conversed to the actual length of the coordinates $(x_{t,i}, y_{t,i})$ and $(x_{t+\Delta t,i}, y_{t+\Delta t,i})$ using the actual size of individual pixel obtained in step (2),
    so the instantaneous velocity of particles is calculated by:

$$V_i = \sqrt{\frac{(x_{t+\Delta t,i} - x_{t,i})^2 + (y_{t+\Delta t,i} - y_{t,i})^2}{\Delta t}},$$

where $\Delta t$ is the time interval between twice exposures.

2. The method according to claim 1, wherein in Step (1), the exposure time of the image sensor is 2.7-3.0 times of the pulse period of the signal generator.

3. The method according to claim 1, wherein in Step (2), a graduated ruler with an accuracy of at least 0.1 mm is used to determine the actual size of individual pixel.

4. The method according to claim 1, wherein the double-exposure image of the same valid particle is identified by a particle matching algorithm in Step (4);
    a particle correlation algorithm is used to conduct time-matching of the particles in the particle matching algorithm.

5. The method according to claim 1, wherein the distribution of the average flow field of the particle velocity in the multiphase system is obtained by means of averaging of the instantaneous velocity based on a particle image containing at least 4000 particles for a period of time.

6. The method according to claim 1, wherein the particle image in Step (1) is an image of anyone selected from the group consisting of bubbles, droplets or solid particles in a multiphase system, or a combination of at least two selected therefrom.

7. The method according to claim 1, wherein the work distance of the telecentric lens is 250-550 mm and the depth of field is 1-3.7 mm.

8. The method according to claim 1, wherein the magnification of the telecentric lens is 0.5-1 time.

9. The method according to claim 1, wherein the external diameter of the telecentric lens is 19-25 mm.

10. The method according to claim 1, wherein the image sensor is a CCD camera or a CMOS camera.

11. The method according to claim 10, wherein the exposure time of the CCD camera or CMOS camera is less than or equal to 1 ms; the resolution is 5-15 μm; the number of pixels in length and width is at least 800×600; the frame frequency is at least 60 fps.

12. The method according to claim 1, wherein the number of the LED lamps is at least 12.

13. The method according to claim 1, wherein the LED lamps are evenly arranged circularly in the package tube;
    the LED lamps are linked with the brightness-adjustable light source through wires.

14. The method according to claim 1, wherein the package tube is composed of a front tube and a back tube with different diameters.

15. The method according to claim 14, wherein the external diameter of the front tube is 25-30 mm and the length is 300-600 mm;
the external diameter of the back tube is 50 mm, and the length is 50 mm;
the material of the package tube is stainless steel.

16. The method according to claim 14, wherein the viewport, LED lamps and telecentric lens are packaged in the front tube; the viewport is arranged on the end of the front tube away from the back tube, followed by the LED lamps and telecentric lens and the image sensor is packaged in the back tube.

17. The method according to claim 1, wherein the viewport is made up of a piece of circular glass coated by antireflection film inside.

18. The method according to claim 1, wherein the signal generator and the image sensor are connected to the controller by a high-speed data line.

19. The method according to claim 1, wherein the display system comprises a LED screen.

20. The method according to claim 1, wherein the signal processing and outputting system, the controller and the display system are integrated into a computer.

* * * * *